(12) United States Patent
Kyllönen

(10) Patent No.: US 7,000,781 B2
(45) Date of Patent: Feb. 21, 2006

(54) FILTERING DEVICE

(75) Inventor: Veikko Kyllönen, Kajaani (FI)

(73) Assignee: Metso Automation OY, Helsinki (FI)

( * ) Notice: Subject to any disclaimer, the term of this patent is extended or adjusted under 35 U.S.C. 154(b) by 245 days.

(21) Appl. No.: 10/265,169

(22) Filed: Oct. 4, 2002

(65) Prior Publication Data

US 2003/0085168 A1 May 8, 2003

Related U.S. Application Data

(63) Continuation of application No. PCT/FI01/00359, filed on Apr. 11, 2001.

(30) Foreign Application Priority Data

Apr. 14, 2000 (FI) .................................. 20000896

(51) Int. Cl.
*B01D 29/44* (2006.01)
*B01D 29/70* (2006.01)
*G01N 1/10* (2006.01)
*G01N 1/34* (2006.01)

(52) U.S. Cl. ...................... 210/354; 210/356; 210/411; 210/488; 73/53.03; 73/53.04; 73/863.23; 73/863.24; 73/863.81

(58) Field of Classification Search ................ 210/357, 210/411, 356, 354, 488; 73/53.03, 53.04, 73/863.24, 863.81, 863.23
See application file for complete search history.

(56) References Cited

U.S. PATENT DOCUMENTS

| 2,959,287 | A | * | 11/1960 | Claude et al. | ............... 210/222 |
|---|---|---|---|---|---|
| 3,006,478 | A | * | 10/1961 | Mueller | ....................... 210/356 |
| 3,221,882 | A | * | 12/1965 | Frantz | ......................... 210/223 |
| 3,622,003 | A | * | 11/1971 | Czech et al. | ................ 210/108 |
| 4,430,232 | A | * | 2/1984 | Doucet | ........................ 210/798 |
| 4,534,388 | A | * | 8/1985 | Pall et al. | ...................... 141/1 |
| 4,655,910 | A | * | 4/1987 | Tabor | ......................... 210/107 |
| 4,804,481 | A | * | 2/1989 | Lennartz | ..................... 210/791 |
| 6,463,816 | B1 | | 10/2002 | Sk.ang.lén | |

FOREIGN PATENT DOCUMENTS

| CN | 1062852 A | 7/1992 |
|---|---|---|
| FI | 57663 | 5/1980 |
| FI | 98096 | 12/1996 |
| SE | 511069 | 8/1999 |
| SU | 1160281 A | 6/1985 |
| SU | 1328724 A1 | 8/1987 |
| WO | WO 00/05562 A1 | 2/2000 |

* cited by examiner

*Primary Examiner*—Thomas M. Lithgow
(74) *Attorney, Agent, or Firm*—Alston & Bird LLP

(57) ABSTRACT

The invention relates to a filtering device for taking a filtrate sample from liquid matter containing solid particles. The filtering device comprises two filter parts and at least one filtering slot between the filter parts. The filter parts are adapted to move in relation to each other in such a manner that the width of the filtering slot changes when the filter parts move in relation to each other. When taking a sample from a process, the filtering slot between the filter parts is at its smallest, and it is adapted to filter the sample while the liquid matter being measured flows from the process to the measurement. When rinsing the filtering device against the sampling direction, the filter parts are adapted to move away from each other, whereby the filtering slot widens.

9 Claims, 3 Drawing Sheets

FILTERING DEVICE

CROSS-REFERENCE TO RELATED APPLICATIONS

This application is a Continuation of International Application PCT/FI01/00359 filed on 11 Apr. 2001, which designated the U.S. and was published under PCT Article 21(2) in English.

FIELD OF THE INVENTION

The invention relates to a filtering device for filtering solid matter particles from liquid matter.

BACKGROUND OF THE INVENTION

In process industry, there is a need to filter suspensions containing liquid and solid matter particles for the purpose of sampling. For instance in paper and pulp industry, filtrate samples are taken from stock for the purpose of monitoring and controlling the process. Stock contains liquid, small amounts of gas, and solid matter particles, such as fibres and possibly slivers. When it is necessary to measure the properties of the liquid in the stock, the solid matter particles are filtered from the sample as well as possible. For this, different filtering devices have been developed, such as those described in published patents FI 57663 and SE 511069, incorporated herein as reference.

In the solution disclosed in FI 57663, the sample is filtered with a screen comprising narrow slots. When the sample is taken, the slots prevent the fibre-like particles from advancing, the liquid flows on to the measurements. When the screen is cleaned, pressurized air is blown towards the process to return the fibres and slivers stuck to the screen to the process. A big problem is, however, that the fibres and slivers are usually so tightly stuck in the slots of the screen that the cleaning is not entirely sufficient. For this reason, the screen is too quickly blocked and needs to be changed. A blocked screen produces a sample slowly.

SE 511069 discloses a sampler comprising a screen which has a slotted surface made of triangular wire. In this screen, too, the fibres and slivers remain in the slots while the liquid flows to the measurement. The screen is cleaned by scraping. This solution, too, has the same problems as that described above. The cleaning is not entirely sufficient, the screen is blocked quite quickly by fibres and slivers and needs to be changed often. A blocked screen produces a sample slowly.

BRIEF DESCRIPTION OF THE INVENTION

It is thus an object of the invention to implement a filtering device for filtrate sampling that is easy to rinse and does not block easily. This object is achieved by a filtering device for filtrate sampling from liquid matter containing solid particles. The filtering device comprises two filter parts and at least one filtering slot between the filter parts; and the filter parts are adapted to move in relation to each other in such a manner that the width of said at least one filtering slot changes when the filter parts move in relation to each other.

Preferred embodiments of the invention are set forth in the dependent claims.

The invention is based on the filtering device having at least one variable-width filtering slot. A narrow filtering slot is used for filtering a sample and during rinsing, the filtering slot of is opened wide so that the solid matter particles stuck to the filtering device would detach from it efficiently.

The filtering device of the invention provides several advantages. The replacing and maintenance intervals of the filtering device are longer, because the filtering device keeps clean. A filtering device that remains clean also allows for a high flow rate of sample.

BRIEF DESCRIPTION OF THE FIGURES

The invention will now be described in more detail by means of preferred embodiments and with reference to the attached drawings, in which.

DETAILED DESCRIPTION OF THE INVENTION

The solution of the invention is suited for use in process industry, where a suspension containing liquid and solid matter particles is filtered to produce a liquid sample. The solution of the invention is especially well-suited for pulp and paper industry, where a filtrate sample is needed from stock. The solution of the invention is, however, not restricted to these applications.

Figure 1:
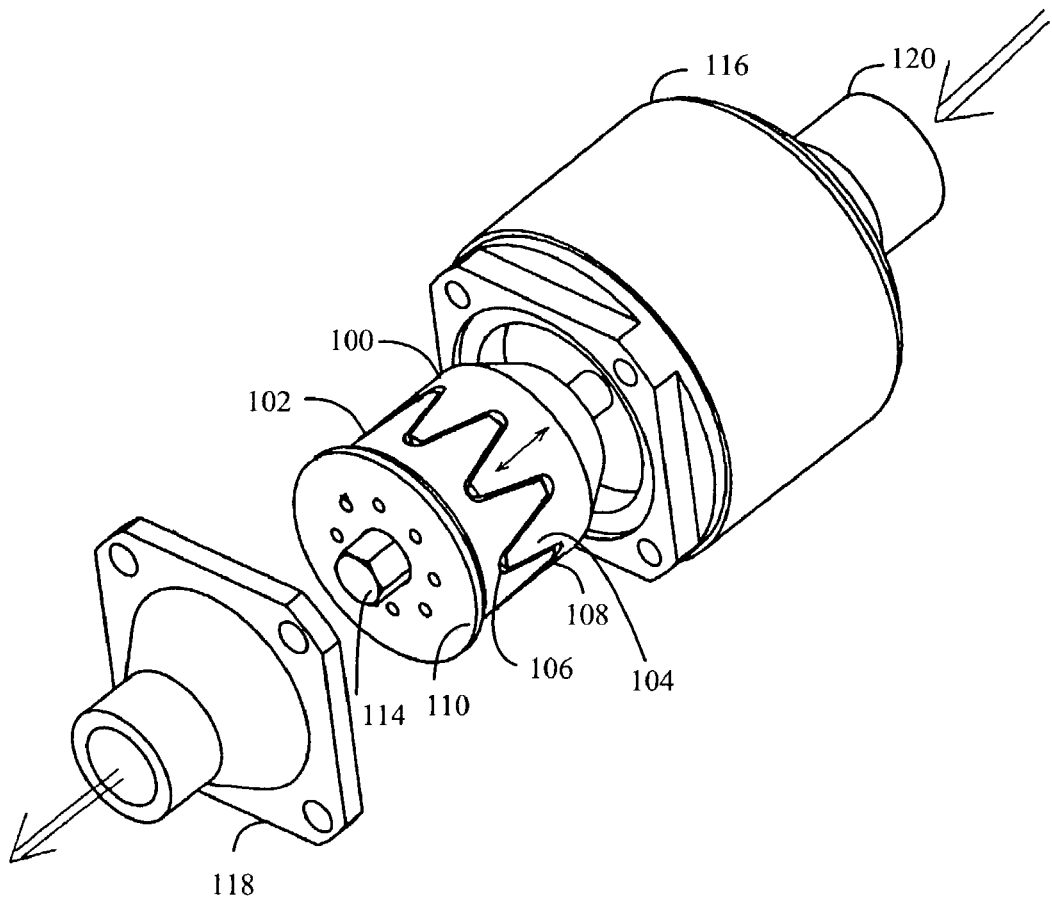
FIG. 1 shows an explosion view of a filtering device.

FIG. 1 shows a possible structure of the filtering device. The flow direction of the sample from the process to measurement is shown by arrows in FIG. 1. The sample is taken for instance from pulp and paper stocks containing slivers and fibres. Two filter parts 100, 102 form the basic structure of the filtering device. The filter parts 100, 102 are located in a body part 116 which fits the filtering device to a sampling pipe 120. The body part 116 can easily be opened for maintenance. The ends of the filter parts 100, 102, which face each other, are fitted to each other in such a manner that when the filter parts 100, 102 are pressed against each other as well as possible, at least one slot 108 remains between the ends of the filter parts 100, 102 and acts as a sample filter. There is a cavity inside the filter parts 100, 102, to which the sample filtered from the body part 116 through the slot 108 flows. From the filter parts 100, 102, the filtered sample flows through at least one opening 112 in an end part 110 and through a pipe adapter 118 to a pipe (not shown in FIG. 1) towards sample measurement. The openings 112 in the end part 110 are designed so that slightly less of the sample can flow through the openings 112 than through the filtering slots 108. This reduces the packing of the solid matter too tightly in the filtering slots 108.

Each filter part 100, 102 comprises at least one guide extension 104 and guide chamber 106, by means of which the filter parts 100, 102 are arranged to centre to each other. This way, the support and centering need caused by the centre axle of the filter parts 100, 102 is reduced in the structure of FIG. 1. The tip of each guide extension 104 touches the narrow bottom area of the guide chamber 106, but since the guide extension 104 is preferably blunt, the guide extension 104 does not necessarily touch the bottom at the sharpest tip of the guide chamber 106. Even though the boundary surface between the filter parts 100, 102 is not straight, each filtering slot is at least approximately straight and of uniform width. A winding boundary surface does, however, produce a long filtering slot 108, which allows for a high sample flow through the filtering slot 108. The disclosed solution produces as much as 10 l/min of sample from pulp industry stock. In such a case, the filtering slot 108 between the filter parts 100, 102 is 0.5 mm, the diameter of the filter parts 100, 102 is 50 mm, and the number of openings in the end part 110 is 4, each opening having a diameter of 4 mm. The filter parts 100, 102 are supported by an axle in the middle of the filter parts, which is protected by a part 114 of the end part 110. The filter parts 100, 102 move in relation to each other in the direction of the axle, which makes it possible for the width of the filtering slot 108 to change when the filter parts 100, 102 move in relation to each other, but the length of the movement is shorter than the depth of the guide chamber 104 so as to maintain the self-steering of the filter parts 100, 102.

Figure 2C:
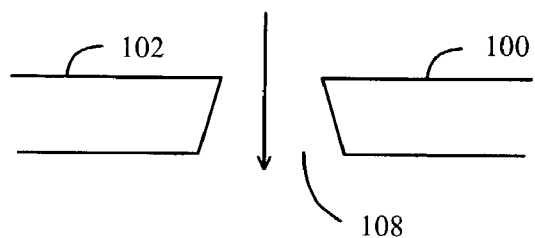
FIG. 2C shows a cross-sectional view of a filtering slot.
Figure 2A:
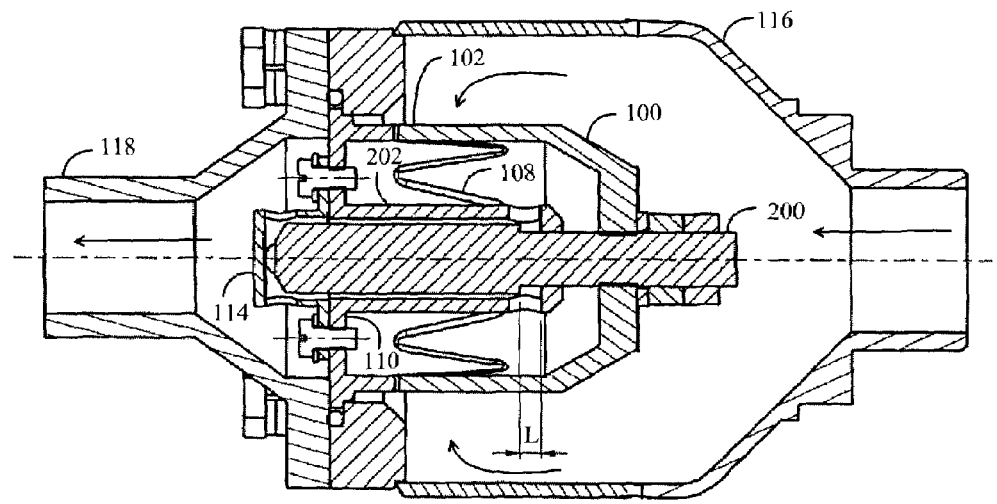
FIG. 2A shows a side projection of the filtering device during sample filtering.

FIG. 2A shows in greater detail the structure of the filtering device by means of a side projection. The arrows show the direction of travel of the sample. The filter parts 100, 102 are in this figure pressed as tightly against each other as possible, whereby the filtering slot 108 is at its smallest. This corresponds to the sampling situation. The axle 200 is attached to the filter part 100 but can move freely in relation to the filter part 102, because the filter part 102 comprises a pipe-like structure 202 inside which the axle 200 is. The filter part 100 is preferably in no way sealed in the pipe-like structure 202 and therefore, the filter part 100 including its axle 200 is very mobile. The axle 200 is preferably a hexagon bar making it possible for the particles to rinse away more easily from between the pipe-like structure 202 and the axle 200. The length of movement of the filter part 100 is limited by a threshold in the axle 200, which does not fit through the end of the pipe-like structure 202 in the filter part 102. The distance L between the threshold of the axle 200 and the end of the pipe-like structure 202 is the longest possible length of movement of the filter part 100 and the axle 200. When filtering pulp industry stock, for instance, the length of movement L can be in millimeters (e.g. 4 mm). The pipe-like structure 202 surrounding the axle 200 has openings at both ends so that the liquid entering the pipe-like structure 202 would flow out efficiently. When sampling a process, the process pressure is adapted to press the filter parts 100, 102 towards each other, in which case the at least one filtering slot 108 between the filter parts 100, 102 is at its smallest. The surface area under pressure of the filter part 100 must then be large enough to allow the pressure difference over the filter part 100 to move the filter part 100 as close as possible to the filter part 102 and to narrow the filtering slot 108 to its smallest.

Figure 2B:
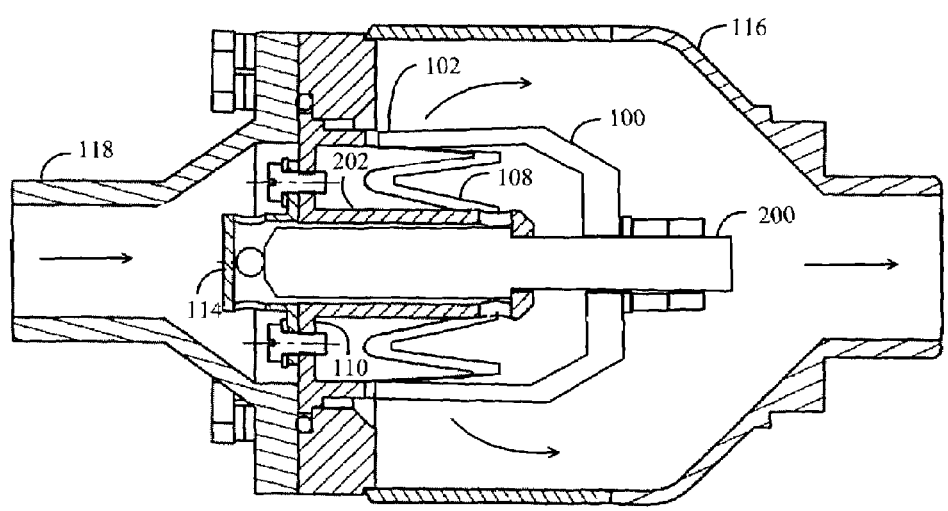
FIG. 2B shows a side projection of the filtering device during rinsing.

In FIG. 2B, the filter parts 100 and 102 are as far away from each other as possible and the filtering slot 108 is at its largest. This corresponds to the situation where the filtering device is being rinsed clean of solid matter accumulated in the filtering slot 108 and around it. The arrows show the direction of rinsing towards the process. When the filtering device is rinsed against the sampling direction, the filter parts 100, 102 move away from each other due to the rinsing pressure. If the rinsing is done towards the process, the rinsing pressure must be higher than the process pressure so that the rinsing pressure can push the filter part 100 away from the filter part 102. The surface area under pressure of the filter part 100 must be large enough to allow the pressure difference over the filter part 100 to move the filter part 100 as far away from the filter part 102 as possible and to widen the filtering slot 108 to its widest.

FIG. 2C shows a cross-sectional view of the filtering slot. The filtering slot 108 between the filter parts 100, 102 preferably widens in the flow direction of the sample (shown with an arrow), which further facilitates detaching the solid matter from the filtering device.

Figure 3:
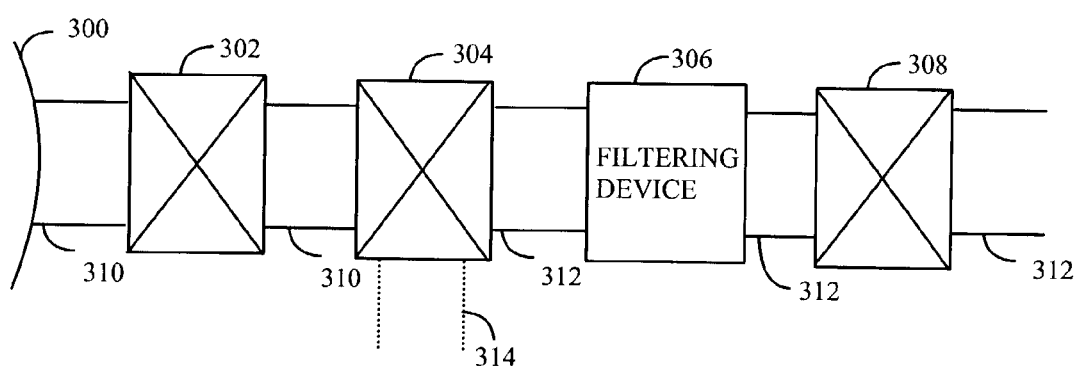
FIG. 3 shows the connection of the filtering device to a stock pipe.

FIG. 3 shows a preferred location of the filtering device in a pulp cooking process, for instance. The stock flows in a pipe 300 in the direction of the paper surface normal. In a continuous process, samples are usually taken periodically through a filtering device 306 in such a manner that between sampling periods, the filtering device is rinsed towards the process. When a sample from the stock is required, valves 302, 304 and 308 are opened. The stock then flows from the pipe 300 through the valves and the filtering device 306 towards sample measurement. When the sample has been taken and is being analysed, the sample and stock remaining in pipes 310 and 312 and the filtering device 306 be rinsed back to the process pipe 300. The rinsing is done for instance with water having a higher pressure than that in the pipe 300. The sample and stock remaining in the pipe 312 and the filtering device 306 can also be rinsed with a lower pressure elsewhere than to the process, if the valve 304 is a three-way valve which directs the rinsing liquid during the rinsing to a pipe 314. The filtering device can also be installed directly into the process pipe without a cut-off valve 302. Using a cut-off valve 302 does, however, allow servicing the filtering device during the process.

In the presented solution, the filtering slot is preferably straight and of uniform width along its entire length, even though the solution of the invention is also implemented by a curved filtering slot of variable width. The width of the filtering slot can be adapted as necessary. When filtering rough slivers away from stock (forward end of a digester), the filtering slots of the filtering device can be bigger than when taking a sample from stock containing a lot of fibres but a small amount of slivers (tail end of a digester).

The filtering device makes it possible to take a sample from the cooking stage to the headbox in all manufacturing phases of a paper and board stock. The filtering device can also be used for filtering pulp, groundwood and refiner stocks. All in all, the filtering device is suited for filtering all paper industry stocks.

The filtering device can be made of any material that endures the properties and conditions (acidity, temperature, pressure, etc.) of the matter being measured. Typically, the filtering device is made of a corrosion-resistant metal, such as stainless steel or titan, without being limited to these, however.

The filter parts 100, 102 can also be magnetised to attract each other, whereby the filter parts 100, 102 remain as close to each other as possible at other times than when the filtering device is rinsed when the rinsing pressure moves the filter parts away from each other. The filter parts can also be made to remain as close to each other as possible by means of a spring or the like pulling the filter parts together.

The presented filtering device need not be pushed in to the sample, instead the sample flows into the filtering device and on to sample measurement through valves. This way, many problems are avoided. In the case of stock flowing in a pipe, pushing the filtering device in to the sample would disturb the stock flow and strong forces would be exerted to the filtering device. At worst, a filtering device located in flowing stock could bend or even break.

Even though the invention has been explained in the above with reference to an example in accordance with the attached drawings, it is obvious that the invention is not restricted to it but can be modified in many ways within the scope of the inventive idea disclosed in the attached claims.

What is claimed is:

1. A littering device, comprising:

opposing duct-shaped filter portions, one of the filter portions having an operable axial end defining a projection and the other of the filter portions having an operable axial end defining a receptacle complementarily configured with respect to and capable of receiving the projection, the operable axial ends of the filter portions being operably engageable such that the projection and the receptacle cooperate to define at least one filtering slot therebetween, the at least one filtering slot being configured to change in width as the filter portions are moved axially in relation to each other, the filter portions being further configured such that a first pressure associated with a filtrate sample received through the at least one filtering slot in a sample flow direction causes tile filter portions to move toward each other so as to minimize the width of the at least one filtering slot, and such that a second pressure associated with rinsing through the at least one filtering slot opposite to the sample flow direction causes the filter portions to move apart and increases the width of the at least one filtering slot so as to facilitate rinsing therefrom of solid particles filtered by the at least one filtering slot.

2. A filtering device as claimed in claim 1, wherein each filter portion comprises at least one guide extension and guide chamber configured to center the filter portions with respect to each other.

3. A filtering device as claimed in claim 2, wherein the filter portions are configured to fit together such that, when the filter portions are pressed against each other, each guide extension presses into the corresponding guide chamber, and the at least one filtering slot is defined between the filter portions.

4. A filtering device as claimed in claim 1, wherein the at least one filtering slot flares in the sample flow direction to facilitate rinsing thereof.

5. A filtering device according to claim 1 wherein the operable axial ends of the filter portions each define a plurality of circumferentially-extending projections such that each operable axial end is sinusoidally-shaped, the sinusoidally-shaped operable axial ends of the filter portions being operably engageable so as to define the at least one filtering slot therebetween.

6. A filtering device according to claim 1 wherein the operable axial ends of the filter portions each define a plurality of regularly spaced and circumferentially-extending projections, the operable axial ends of the filter portions being operably engageable so as to define the at least one filtering slot therebetween.

7. A filtering device according to claim 1 wherein the filter portions are further configured to receive a filtrate sample for a measurement through the at least one filtering slot from a process using liquid matter containing solid particles and to axially discharge the filtrate sample from at least one of the filter portions, the filter portions also being configured to cooperate such that the at least one filtering slot is capable of receiving a greater amount of the filtrate sample than an amount of the filtrate sample capable of being discharged axially from the at least one of the filter portions so as to reduce packing of the solid particles in the at least one filtering slot.

8. A filtering device according to claim 7 wherein the at least one of the filter portions baying the filtrate sample discharged therethrough is further configured to define at least one aperture, the at least one aperture being configured to define a smaller area than an area defined by the at least one filtering slot such that the greater amount of the filtrate sample is capable of being received than discharged.

9. A filtering device according to claim 1 wherein the filter portions are magnetized to attract each other such that the filter portions are maintained close to each other so as to minimize the width of the at least one filtering slot other than when rinsing.

\* \* \* \* \*

UNITED STATES PATENT AND TRADEMARK OFFICE
CERTIFICATE OF CORRECTION

PATENT NO. : 7,000,781 B2  Page 1 of 1
APPLICATION NO. : 10/265169
DATED : February 21, 2006
INVENTOR(S) : Kyllönen It is certified that error appears in the above-identified patent and that said Letters Patent is hereby corrected as shown below:

Column 5,
Line 2, "littering" should read --filtering--.
Line 17, "tile" should read --the--.

Column 6,
Line 26, "baying" should read --having--.

Signed and Sealed this

Seventh Day of November, 2006

JON W. DUDAS
*Director of the United States Patent and Trademark Office*